United States Patent
Sattig et al.

(10) Patent No.: US 10,293,987 B2
(45) Date of Patent: May 21, 2019

(54) CLOSURE FOR PHARMACEUTICAL CONTAINERS AND METHOD FOR SEALING A BOTTLE

(71) Applicant: aap Biomaterials GmbH, Dieburg (DE)

(72) Inventors: Christoph Sattig, Dieburg (DE); Stefan Deusser, Karlstein (DE); Rike Anders-Wessel, Oberursel (DE)

(73) Assignee: OSARTIS GmbH, Dieburg (DE)

( * ) Notice: Subject to any disclaimer, the term of this patent is extended or adjusted under 35 U.S.C. 154(b) by 83 days.

(21) Appl. No.: 15/325,999

(22) PCT Filed: Jun. 18, 2015

(86) PCT No.: PCT/EP2015/063727
§ 371 (c)(1),
(2) Date: Jan. 12, 2017

(87) PCT Pub. No.: WO2016/012165
PCT Pub. Date: Jan. 28, 2016

(65) Prior Publication Data
US 2017/0349335 A1    Dec. 7, 2017

(30) Foreign Application Priority Data

Jul. 22, 2014    (DE) .................. 10 2014 110 327

(51) Int. Cl.
*B65D 41/20*    (2006.01)
*A61J 1/14*    (2006.01)
(Continued)

(52) U.S. Cl.
CPC ........ *B65D 41/205* (2013.01); *A61B 17/8833* (2013.01); *A61J 1/1406* (2013.01);
(Continued)

(58) Field of Classification Search
CPC ...... A61J 1/1425; A61J 1/1412; A61J 1/1406; A61J 1/05; A61J 1/201; B65D 51/002; B65D 2251/0015; B65D 51/20
See application file for complete search history.

(56) References Cited

U.S. PATENT DOCUMENTS 5,100,009 A * 3/1992 Thompson ............. B21D 51/30
215/341
5,188,628 A * 2/1993 Rani .................... B65D 51/002
215/248

(Continued)

FOREIGN PATENT DOCUMENTS

BE           538395 A    5/1955
DE    10 2009 004 235 A1    7/2010
(Continued)

OTHER PUBLICATIONS

"International Search Report and Written Opinion" issued in counterpart PCT Application No. PCT/EP2015/063727, dated Sep. 24, 2015.
(Continued)

*Primary Examiner* — Shawn M Braden
(74) *Attorney, Agent, or Firm* — Kaplan Breyer Schwarz, LLP

(57) ABSTRACT

A closure for a pharmaceutical vial. The closure comprises an aluminum foil with an inductively meltable adhesive, an elastic seal, and a cap. The cap has an opening through which a perforating cannula can be inserted.

13 Claims, 6 Drawing Sheets

(51) Int. Cl.
  *A61B 17/88* (2006.01)
  *B65B 3/00* (2006.01)
  *B65B 7/16* (2006.01)
  *B65B 7/28* (2006.01)
  *B65B 51/22* (2006.01)
  *B65B 55/10* (2006.01)
  *B65D 41/16* (2006.01)
  *B65D 45/16* (2006.01)
  *B65D 53/06* (2006.01)

(52) U.S. Cl.
  CPC .......... *A61J 1/1425* (2015.05); *A61J 1/1431* (2015.05); *B65B 3/003* (2013.01); *B65B 7/161* (2013.01); *B65B 7/2871* (2013.01); *B65B 7/2878* (2013.01); *B65B 51/227* (2013.01); *B65B 55/10* (2013.01); *B65D 41/16* (2013.01); *B65D 45/16* (2013.01); *B65D 53/06* (2013.01); *A61B 2017/8838* (2013.01)

(56) References Cited

U.S. PATENT DOCUMENTS

| | | | | |
|---|---|---|---|---|
| 5,332,113 A * | 7/1994 | Kusler, III | ............ | A61J 1/1406 215/232 |
| 5,662,230 A | 9/1997 | Finneran | | |
| 9,186,635 B2 * | 11/2015 | Bielenstein | ............ | B01F 7/007 |
| 9,211,978 B2 * | 12/2015 | Fox | ............ | B65D 41/045 |
| 9,668,939 B2 * | 6/2017 | Carrel | ............ | A61J 7/0472 |
| 2010/0089862 A1 * | 4/2010 | Schmitt | ............ | B65D 51/002 215/249 |
| 2013/0333796 A1 * | 12/2013 | Py | ............ | B65D 51/002 141/1 |
| 2015/0084253 A1 * | 3/2015 | Dallman | ............ | A61J 1/16 269/5 |

FOREIGN PATENT DOCUMENTS

| | | |
|---|---|---|
| EP | 569835 A1 | 11/1993 |
| EP | 1435254 A2 | 7/2004 |
| WO | 2010105807 A1 | 9/2010 |
| WO | 2014104027 A1 | 3/2014 |

OTHER PUBLICATIONS

Authorized Officer: Nora Lindner, "International Preliminary Report on Patentability" issued in co-pending PCT application No. PCT/EP2015/063727, dated Jan. 24, 2017, Publisher: PCT.

Authorized Officer: Nora Lindner, "English Translation of the International Preliminary Report on Patentability" issued in co-pending PCT application No. PCT/EP2015/063727, dated Feb. 2, 2017, Publisher: PCT.

* cited by examiner

CLOSURE FOR PHARMACEUTICAL CONTAINERS AND METHOD FOR SEALING A BOTTLE

FIELD OF THE INVENTION

The invention relates to a closure for bottles or vials, and also relates to a method for sealing a vial. In particular, the invention relates to a closure which is intended for hermetically sealed packages in the field of medical technology and pharmacology, more particularly for the liquid component of a bone cement.

BACKGROUND OF THE INVENTION

In the pharmaceutical sector, liquid substances are often stored in glass ampoules. Such liquid substances, for instance in particular the liquid component of a bone cement, might be volatile, chemically aggressive, or toxic.

Therefore, glass ampoules are particularly suitable for such liquids, since they are chemically stable and at the same time impermeable to gases and liquids, so that only very small amounts, if any, of components of the liquid stored in the ampoule will exit from the package, or only very small amounts, if any, of gases such as oxygen will enter into or exit from the package that is formed when the latter consists of a glass body sealed by flame-melting, such as an ampoule, for example.

Such an ampoule can for instance be used to store the monomer component of a bone cement, such as methyl methacrylate, for several years without loss. This is achieved in glass ampoules that have a neck which must be broken before extraction.

However, such break-open ampoules are not optimal in handling. For example, slivers might be produced implying a risk of injuries for the user or contamination of the liquid. Furthermore, the extraction of the liquid for example by means of a syringe is complicated and entails an elevated risk for the ampoule to be held inclined to such an extent that liquid drips down or that the quantity of the extracted liquid is inaccurate or injuries may be caused.

Furthermore, packages are known which are sealed with a septum. Such a septum usually consists of an elastomeric layer, which is crimped onto the collar of a vial with an aluminum crimping cap.

Such packages have the advantage that they can be perforated, for example using a hollow needle, in order to extract the liquid. Once the hollow needle has been retracted, the septum closes so that there is at most a slight risk for further liquid to inadvertently escape from the package or for contaminants to enter the package.

However, it has been found that such closures are not sufficiently impermeable for many applications, even if high-quality multi-layer seals are used. Over the storage period, evaporation of the liquid contents occurs.

For example the monomer component of a bone cement, such as methyl methacrylate for example, will outgas which implies a loss of liquid. Besides inaccurate dosing, this may also cause an unintentional partial reaction of the powder component if the liquid component and the solid component are stored side by side in a packaging.

Another problem is insufficient impermeability to gases that might enter the vial and react with the contents. This may also pose a problem when the package is sterilized exteriorly using a gas. In particular highly toxic ethylene oxide is used for sterilization of the package, which must not get into the package, under no circumstances, even not in small quantities.

OBJECT OF THE INVENTION

Given this background, the invention is based on the object of at least mitigating the aforementioned drawbacks of the prior art.

More particularly, it is an object of the invention to provide a package for storing fluids, which can be handled safely and which has a closure with high impermeability to gases.

SUMMARY OF THE INVENTION

The object of the invention is already achieved by the closure and method in accordance with an illustrative embodiment of the present invention.

The invention relates to a closure which is especially intended for application for medical pharmaceutical packages.

The closure comprises a cap made of a dielectric material, in particular of a polymer, which can be applied on a vial.

In the context of the invention, vial in particular refers to glass vials which have a collar.

However, it is also conceivable to use the invention for other types of vials, also for larger packages. It is potentially also conceivable to use the invention for vials made of materials other than glass, in particular for plastic vials. However, the vial should be made of a dielectric material, i.e. not of an electrically conductive material such as metal.

The closure comprises a metal foil inserted into the cap, which in the assembled state of the closure rests on a rim of the vial. Preferably, an aluminum foil is used as the metal foil. The latter preferably rests on the collar of a vial.

At least the area of the metal foil which rests on the rim of the vial is provided with an adhesive, in particular an adhesive polymer which can be melted inductively via the metal foil, by heating the foil material.

Such aluminum seals which can be applied using an inductively heatable hot-melting adhesive are basically known from the prior art.

These are in particular aluminum foils which are coated with a thermoplastic polymer which is approved according to FDA 21 CFR § 177.1330.

An elastic seal is inserted above the metal foil, that is to say between the base wall of the closure and the metal foil, and due to this seal the metal foil is already sealingly pressed onto the rim of the vial once the cap has been applied to the vial, and this without the vial having been inductively sealed yet at this time by heating the metal foil and melting the adhesive.

The invention therefore relates to a closure with an inductively attachable aluminum seal which already seals to the extent to be liquid-tight under normal situations as soon as the closure has been applied.

Furthermore, the base wall of the cap has at least one opening through which the elastic seal and the metal foil can be perforated.

Also conceivable is the use of so-called flip-off caps which have a removable additional cover over the opening.

The elastic seal ensures tight engagement of the metal foil during inductive sealing. The contact force may furthermore be intensified or limited by the sealing tool.

Furthermore, the elastic seal functions as a septum.

Therefore, the invention provides a package comprising a closure that can be perforated with a hollow needle in order to extract liquid and which under normal situations is at least liquid-tight after removal of the hollow needle.

The inventors have found that adequate sealing can be achieved only by an aluminum seal which is provided with an inductively heatable hot-melting adhesive, so that highly volatile substances such as for example methyl methacrylate which is an organic solvent can be stored over extended periods without escaping and without the risk that during sterilization with a gas such as ethylene oxide the latter penetrates into the package.

The closure is preferably designed as a snap-on closure. These are closures which are usually urged over a collar, wherein the closure is made of a polymer which is elastic to the extent that it stretches until being slid over the largest portion of the neck finish of the vial. Preferably, such plastic materials have a yield strength of at least 5% according to ISO 527-2.

The cap is preferably designed so that it cannot be removed without being destroyed, or only when a special tool is used.

For example, claws that become latched below the collar of a vial may be beveled on one end in order to slide over the collar, while the opposite side engages on the collar so that the cap will be destroyed if it is pulled off by force.

In a preferred embodiment of the invention, the elastic seal is rotatable relative to the metal foil.

That means, in the non-applied state the seal and the metal foil are loosely superimposed. However, it is also conceivable to provide for instance a wax between the metal foil and the elastic seal, which melts away during inductive melt-bonding and then allows the metal foil and the elastic seal to be rotated relative to one another.

Due to the fact that in the applied state the metal foil and the elastic seal are not firmly connected to one another, for example glue-connected, there is no risk for the metal foil to become damaged when the cap is rotated, or to become detached from the rim of the housing.

It is moreover conceivable to provide an additional elastic layer on the surface of the elastic seal that engages the metal foil, for example a polytetrafluoroethylene layer or the like.

In order to be effective as a septum and to develop a sufficient contact force against the metal foil, the elastic seal of a preferred embodiment of the invention has a thickness from 0.1 to 5 mm, particularly preferably from 2 to 4 mm.

The elastic seal may be made of a variety of possible materials that are conceivable, in particular silicone is used. More particularly, a material is used which has a Shore A hardness from 20 to 80, in particular from 30 to 60.

In one embodiment of the invention, the cap and/or the elastic seal is at least partially made of a transparent material.

This embodiment of the invention in particular permits visual quality inspection insofar as the aluminum seal is now visible and can be visually checked, in particular even using a camera, as to whether it rests on the rim over the entire circumference thereof or whether it exhibits folds or bends.

In one embodiment of the invention, the cap has claws for being latched on a collar of the vial, the claws being distributed around the circumference of the cap covering a maximum of 180° in total.

This embodiment of the invention provides for simplified manufacturing, in particular of a snap-on closure for which the cap can be rotated and ejected from the mold after injection molding.

For example, three claws may be provided evenly distributed around the circumference, each claw extending over a circumferential arc corresponding to not more than 60°.

In a further embodiment of the invention, the cap comprises claws, and openings are provided in the base wall of the cap above the claws. Thus, the claws of the injection mold can be formed in a simple manner by means of a slider.

However, it is also conceivable to use the openings for inserting a demolding tool or a tool that is used to apply the closure.

In a preferred embodiment of the invention, the claws additionally serve to retain the metal foil and the elastic seal.

Due to their elasticity, the elastic seal and the metal foil can be urged into the cap, but will then be prevented from falling out by the claws. This allows to apply the closure in only one station.

The invention in particular relates to packages which are filled with a monomer for autopolymerization, in particular with a bone cement monomer.

For example, the invention also relates to the use of the package for a mixing device for bone cement.

Such a mixing device for bone cement is known from published patent application WO 2010/105807 A1, for example. In such a device, the monomer vial is emptied, for example by being perforated using a hollow needle, and the liquid enters into a mixing chamber where it is mixed with the solid component of the bone cement.

The invention further relates to a method for sealing a vial with a closure described above, the method comprising first filling the vial, then applying the closure, and subsequently heating the metal foil by induction so that the adhesive melts whereby a material bond is produced between the metal foil and a rim of the vial.

In particular snap-on closures can be applied automatically in a short time, which increases the throughput of the machine.

The sealing of the metal foil by inductive heating may be performed either directly after the application or at a later point in time, since according to a preferred embodiment of the invention the vial will already be sealed in a liquid-tight manner by the mere application of the closure. The sterile barrier for sterile filled liquids is provided by the metal foil.

It is furthermore conceivable to use a screw closure instead of a snap-on closure. In this case it is possible to employ a peelable aluminum seal.

The gas-tight seal existent once the inductive sealing has been accomplished makes subsequent sterilization possible, even if a toxic gas such as ethylene oxide is used, without incurring the risk that the gas penetrates into the vial.

The filling of pharmaceutical vials generally takes place in an aseptic machine area. For cost and safety reasons it is generally desired to keep this area as small as possible.

The invention makes it possible to perform the inductive sealing in an area downstream of the aseptic area.

The inductive sealing may in particular be accomplished so rapidly that the vials on a conveyor need not have to be stopped but can be sealed contactless while being conveyed past the machine.

In addition to its function as a gas-tight seal and optionally as a sterile barrier, the metal foil, in particular the aluminum foil, moreover functions as a barrier to organic solvents and in particular prevents the release of solvents, for example from the elastic seal.

DETAILED DESCRIPTION

The invention will now be explained in more detail by way of exemplary embodiments and with reference to the drawings of FIGS. 1 to 10.

Figure 1:
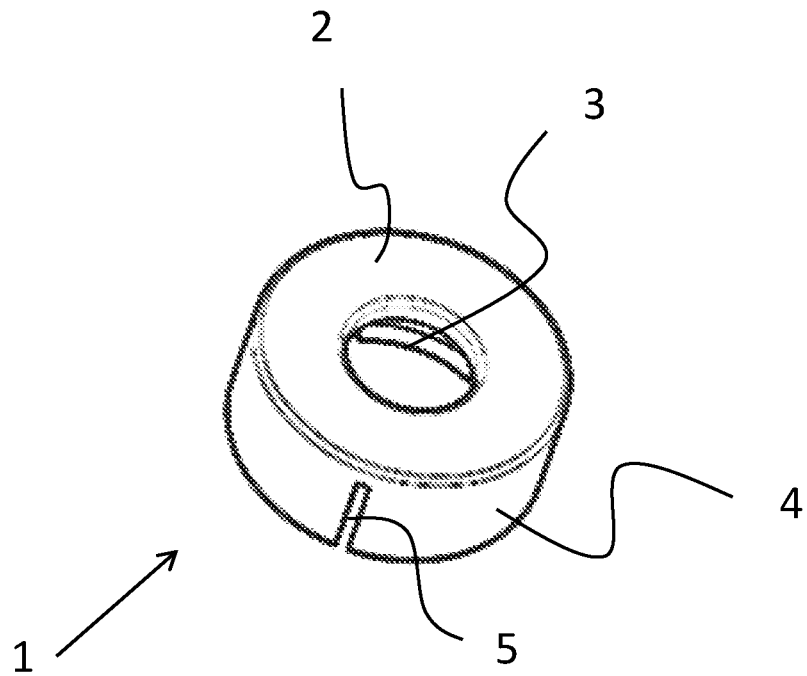
FIG. 1 shows a perspective view of a cap which is intended for a closure.

FIG. 1 shows a perspective view of a cap 1 which is intended for a closure according to the invention.

Cap 1 is designed as a snap-on closure and has a substantially circular cross section.

The base wall 2 of the cap has a central opening 3 through which for instance a hollow needle can be inserted into the closure.

However, the base wall 2 of the cap adjacent to the opening 3 should at least extend so as to cover the rim of the vial (not shown).

Cap 1 has a circular cylindrical basic shape.

The lateral wall 4 of cap 1 is provided with at least one slot 5 which has the effect that the individual segments of lateral wall 4 can deflect outwards more easily when the cap is applied.

The aluminum foil and the elastic seal are not inserted in this view.

Figure 2:
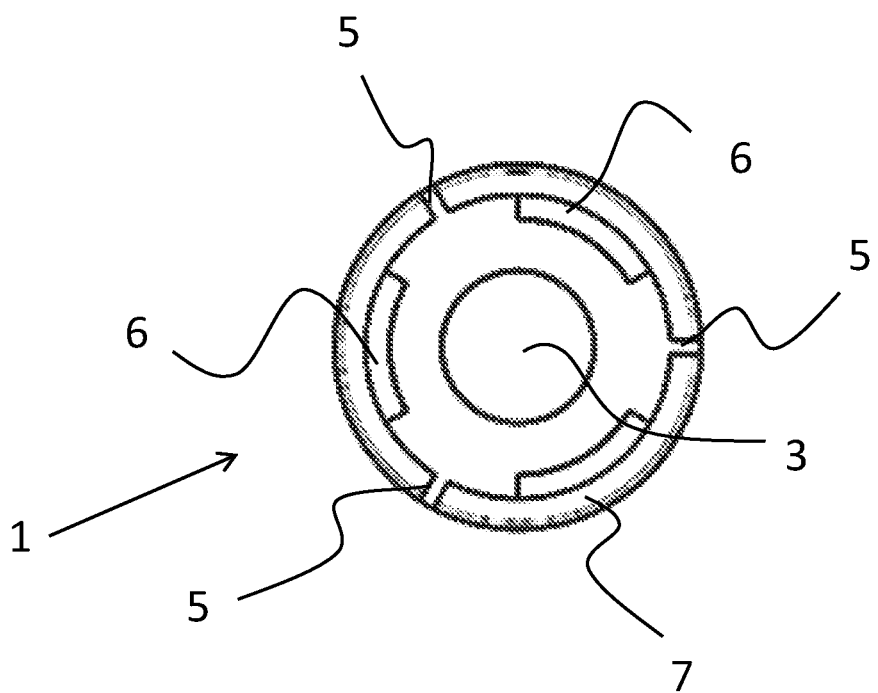
FIG. 2 is a bottom view of the cap illustrated in FIG. 1.

FIG. 2 is a bottom view of the cap 1 illustrated in FIG. 1. Central opening 3 is visible. Moreover, three claws 6 can be seen in this view, which extend inwards from the lower end 7 of the lateral wall and which are latched below the collar of a vial in the assembled state.

Claws 6 extend over less than 180° of the circumference of cap 1 in total.

This has the advantage, inter alia, that when the cap 1 is manufactured by injection molding, it can be demolded by rotating the cap.

Claws 6 are distributed uniformly around the circumference, and a slot 5 is provided between each pair of adjacent claws. In the present exemplary embodiment, the slot extends over at least half of the height of the lateral wall (4 in FIG. 1).

Figure 3:
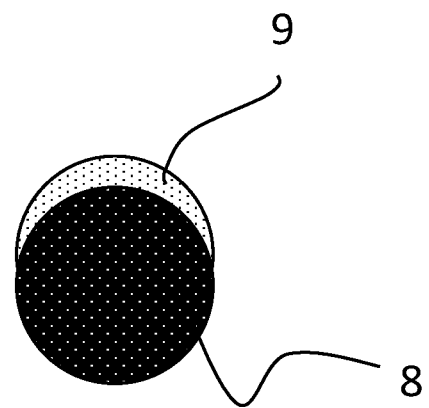
FIG. 3 schematically illustrates an elastic seal.

FIG. 3 schematically illustrates an elastic seal 8, for example made of silicone, and an aluminum foil 9, which are intended to be inserted into the cap.

Elastic seal 8 and aluminum foil 9 are not tightly connected, for example not glued together.

Figure 4:
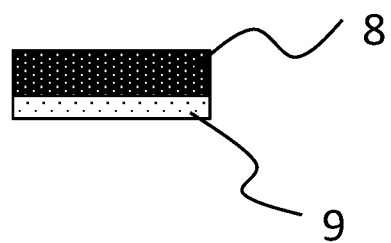
FIG. 4 shows the elastic seal and an aluminum foil superimposed and covering both the rim of a vial onto which they are applied.

As can be seen in FIG. 4, the elastic seal 8 and the aluminum foil 9 are superimposed and cover both the rim of a vial onto which they are applied as well as the entire mouth opening of the vial.

Aluminum foil 9 is provided with an adhesive (not shown) on its lower surface.

In this manner, the aluminum foil provides an inductively applicable seal insofar as the aluminum foil is heated inductively so that the adhesive melts and a material bond is produced between the rim of the vial and the aluminum foil.

Figures 5, 6:
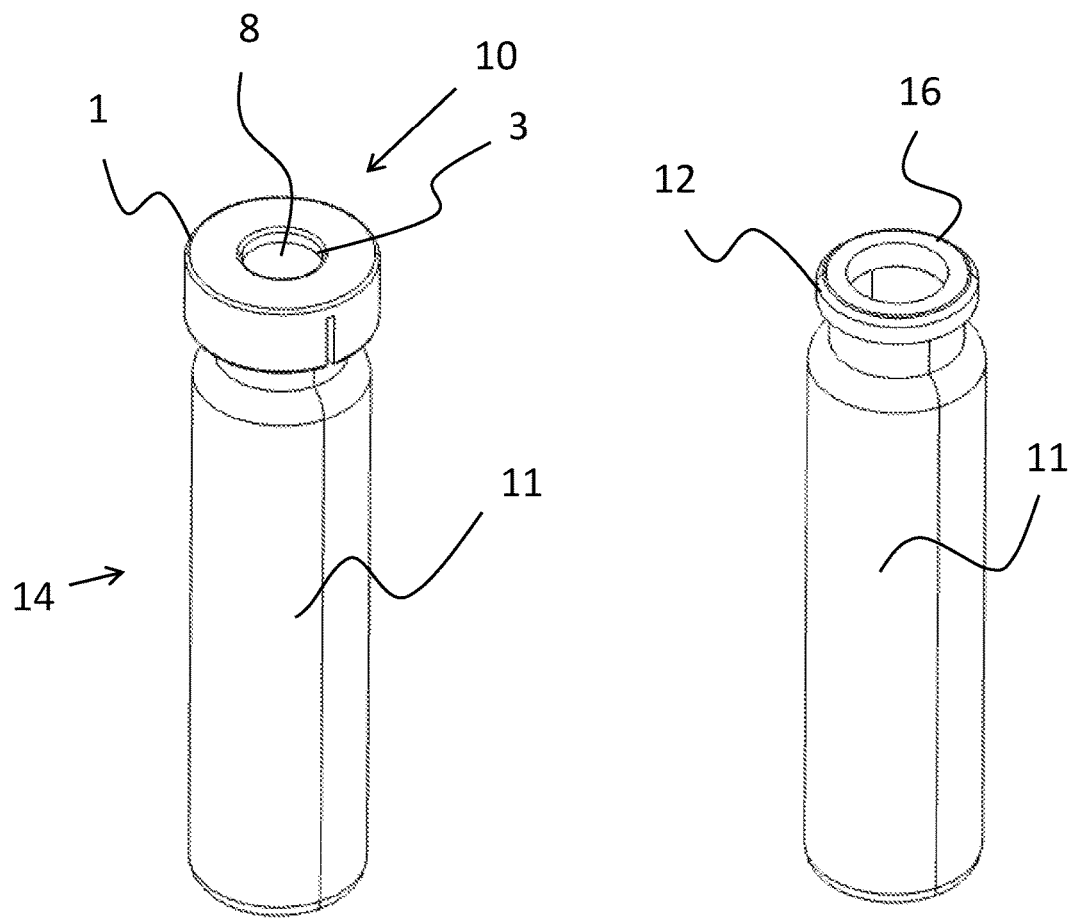
FIG. 5 shows a perspective view of a package for a liquid.
FIG. 6 shows the vial with the cap removed.

FIG. 5 shows a perspective view of a package 14 for a liquid (not shown).

In this exemplary embodiment, package 14 consists of a circular cylindrical vial 11 and of the closure 10 which comprises the cap 1 as shown in FIGS. 1 and 2 and an aluminum foil and an elastic seal 8.

FIG. 6 shows the vial 11 with the cap removed.

It can be seen that the vial has a collar 12.

The upper end of collar 12 defines the rim on which the aluminum foil rests in its applied state.

The claws of the cap latch below the underside of collar 12.

Figure 7:
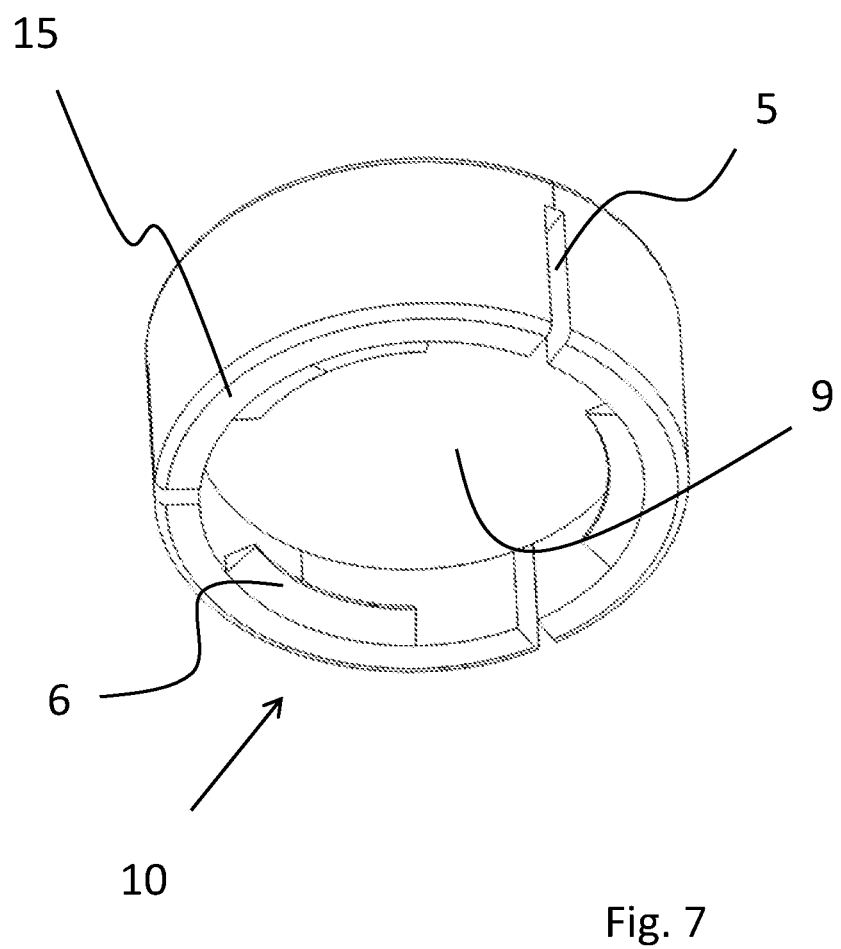
FIG. 7 shows a perspective view of a closure.

FIG. 7 is a perspective view of a closure.

It comprises the cap as illustrated in FIGS. 1 and 2, which has slots 5 provided in the lateral wall and claws adjacent to the lower end 15, which are intended for being latched below the collar of a vial.

The elastic seal and the aluminum foil 9 are now inserted here. The aluminum foil can be seen.

Once inserted, the aluminum foil 9 and the elastic seal (not shown) are retained in the cap by the claws 6.

The closure of the invention can thus be introduced into a machine as a preassembled component and can be applied automatically in a single processing step.

This view clearly shows that the claws 6 are in the form of wedges projecting inwardly from the circular circumferential shape of the cap.

Furthermore, the wedge-shaped claws 6 are beveled at their lower end so as to slide over the collar of a vial when being applied. In this case the lateral wall is able to slightly deflect due to the slots 5.

On their upper end, by contrast, the claws extend substantially horizontally in the present exemplary embodiment.

This configuration has the consequence that the cap will be destroyed if it is forcible withdrawn.

Figure 8:
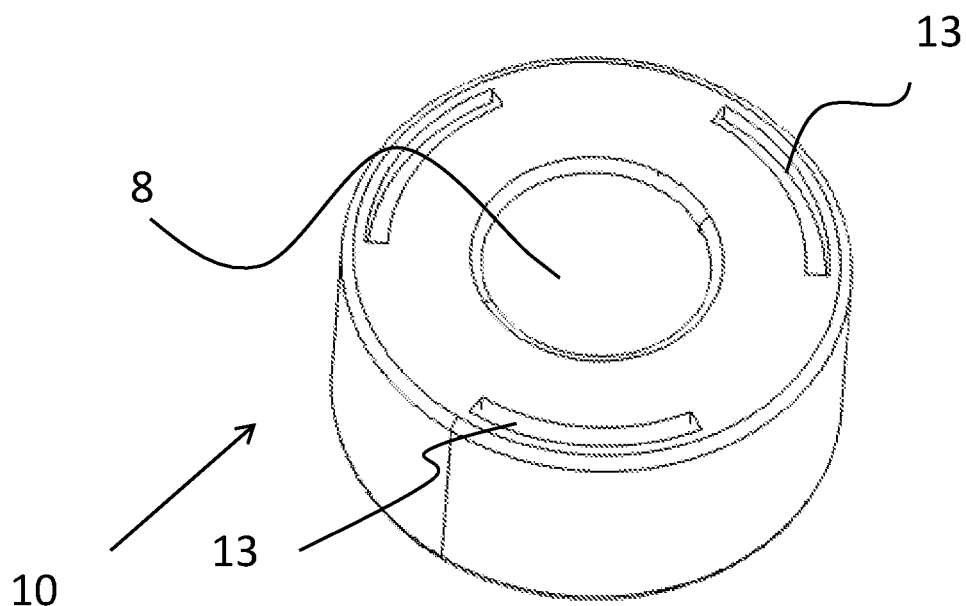
FIG. 8 shows an alternative embodiment of a closure.

FIG. 8 shows an alternative embodiment of a closure.

It essentially corresponds to the previously illustrated closure, with the difference that openings 13 are provided in the base wall, which are located above the claws.

The openings follow the circular extension of the cap.

Furthermore, this embodiment variant has no slots in the lateral wall.

For this embodiment, a suitable material with increased yield strength has to be selected.

The elastic seal 8 can be seen through the opening of the cap.

However, it will be understood that it is conceivable to provide further layers above the elastic seal without thereby impairing the function of the closure.

Figure 9:
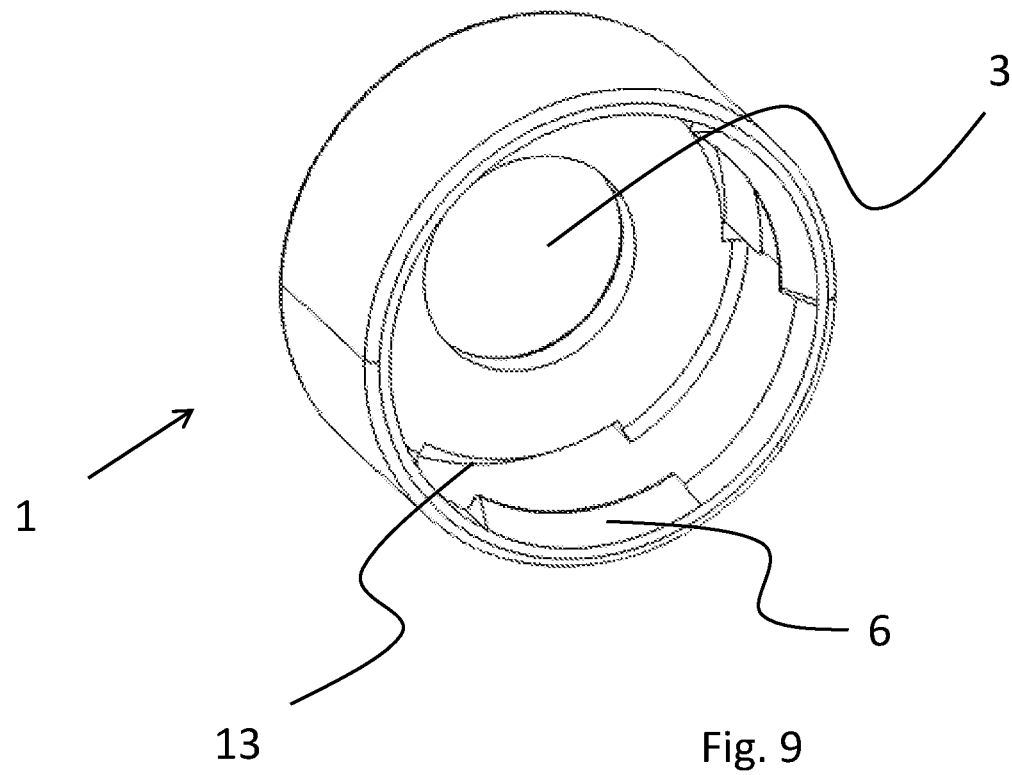
FIG. 9 shows a perspective bottom view of the cap used for the closure illustrated in FIG. 8.

FIG. 9 shows a perspective bottom view of the cap 1 used for the closure illustrated in FIG. 8.

The central opening can be seen. Furthermore, claws 6 can be seen, which are similar to those of the embodiment variant illustrated before and which occupy only part of the circumference of the cap.

In addition to their function for demolding the cap, claws which do not extend along the entire circumference have the advantage of reducing the risk for inclusion of gas. Thus, during sterilization the gas can enter unhindered between the cap and the vial and then re-escape. The gas barrier is alone formed by the aluminum seal.

It can furthermore be seen here that the openings 13 which are provided above the claws 6 essentially correspond to the claws 6 in terms of their shape and location.

Figure 10:
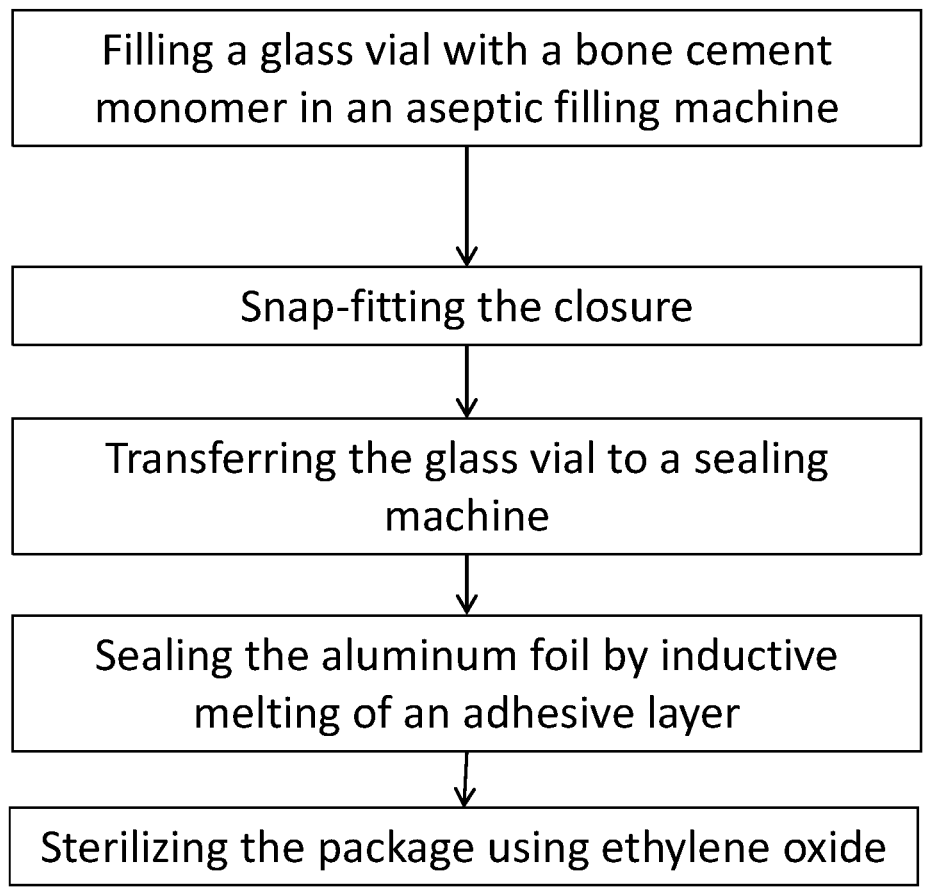
FIG. 10 is a flow chart for using the cap according to the invention for sealing a vial.

Now referring to the flow chart of FIG. 10, the use of the cap according to the invention for sealing a vial will be explained by way of example.

First, a glass vial is filled with a bone cement monomer in an aseptic filling machine, and the closure according to the invention, for example the closure illustrated above, is applied by snap-fitting within the aseptic filling machine.

The snap-fitting process is automated.

Then, the glass vial is transferred, for example on a conveyor, into a sealing machine for the purpose of inductively sealing the aluminum seal. This sealing machine need not necessarily be arranged in the aseptic area, since after snap-fitting of the closure the vial is already closed in liquid-tight manner and largely provides a sterile barrier.

Then, the aluminum foil is sealed by inductive melting of the adhesive layer and then forms a gas barrier which prevents the penetration of gas and ensures that highly volatile substances can be stored over elongated periods of time.

Subsequently, the package is sterilized using ethylene oxide, prior to packaging.

The invention permits for the first time to provide a package with a septum for a perforating cannula in which even highly volatile substances can be stored over elongated periods of time.

LIST OF REFERENCE NUMERALS

1 Cap
2 Base wall
3 Opening
4 Lateral wall
5 Slot
6 Claw
7 Lower end
8 Elastic seal
9 Aluminum foil
10 Closure
11 Vial
12 Collar
13 Opening
14 Package
15 Lower end
16 Rim

What is claimed is:

1. A closure for pharmaceutical packages, comprising:
a cap made of a dielectric material and attachable on a vial;
a metal foil which in its assembled state rests on a rim of said vial, wherein at least on a surface that rests on the rim the metal foil is provided with an adhesive which is meltable inductively through the metal foil; and
an elastic seal inserted above the metal foil;
wherein the cap has a base wall with at least one opening through which the elastic seal and the metal foil can be perforated;
wherein the elastic seal is adapted so that once the cap has been applied on the vial the metal foil is already sealingly pressed onto the rim of the vial without the adhesive having been melted yet; and
wherein the closure is a snap-on closure.

2. The closure as claimed in claim 1, wherein the snap-on closure is designed so that it cannot be removed without being destroyed.

3. The closure as claimed in claim 1, wherein the metal foil is an aluminum foil.

4. The closure as claimed in claim 1, wherein the elastic seal is rotatable relative to the metal foil.

5. The closure as claimed in claim 1, wherein the cap or the elastic seal is made of a transparent material.

6. The closure as claimed in claim 1, wherein the cap has claws for being latched on a collar of the vial, wherein the claws are distributed around the circumference of the cap covering a maximum of 180° in total.

7. The closure as claimed in claim 1, wherein the cap has claws for being latched on a collar of the vial, and wherein the cap has openings in its base wall above the claws.

8. The closure as claimed in claim 1, wherein the cap has claws for being latched on a collar of the vial, wherein the metal foil and the elastic seal are retained in the cap by the claws.

9. A package comprising a vial with a closure as claimed in claim 1.

10. The package as claimed in claim 9, wherein the package is filled with bone cement monomer.

11. A mixing device for bone cement, comprising a package according to claim 10, which is filled with bone cement monomer.

12. A method for sealing a vial with a closure for pharmaceutical packages which comprises
a cap made of a dielectric material and attachable on a vial;
a metal foil which in its assembled state rests on a rim of said vial, wherein at least on a surface that rests on the rim the metal foil is provided with an adhesive which is meltable inductively through the metal foil; and
an elastic seal inserted above the metal foil;
wherein the cap has a base wall with at least one opening through which the elastic seal and the metal foil can be perforated; and
wherein the method comprises the steps of:
filling the vial;
then applying the closure in an aseptic area, wherein the vial is already sealed when the closure is applied; and
subsequently heating the metal foil by induction so that the adhesive melts thereby creating a material bond between the metal foil and a rim of the vial, wherein the inductive heating of the metal foil is performed after leaving the aseptic area.

13. The method for sealing a vial as claimed in claim 12, wherein after the material bond has been created between the metal foil and the rim, the vial is sterilized externally using a gas.

* * * * *